United States Patent [19]
Tanaka et al.

[11] Patent Number: 4,937,265
[45] Date of Patent: Jun. 26, 1990

[54] ANTIDIABETIC METHOD COMPRISING 7-THIAPROSTAGLANDIN $E_1$ OR ITS DERIVATIVES

[75] Inventors: Toshio Tanaka, Hino; Yukio Motoyama, Suita, both of Japan

[73] Assignees: Teijin Limited; Fujisawa Pharmaceutical Company, Ltd., both of Osaka, Japan

[21] Appl. No.: 195,133

[22] Filed: May 17, 1988

[30] Foreign Application Priority Data

May 28, 1987 [JP] Japan ................... 62-129984

[51] Int. Cl.$^5$ ................... A61K 31/19; A61K 31/215; A61K 31/557
[52] U.S. Cl. ................... 514/530; 514/573; 514/866
[58] Field of Search ................... 514/530, 573, 866

[56] References Cited

U.S. PATENT DOCUMENTS 4,080,458  3/1978  Radunz et al. ................... 514/573 X

OTHER PUBLICATIONS

Chemical Abstracts 99:212335g (1983).
Chemical Abstracts 104:168262b (1986).
Chemical Abstracts, vol. 108, 107025n (1988).
Biochemical and Biophysical Research Communications, vol. 150, pp. 225–230, (1988).

Primary Examiner—Leonard Schenkman
Attorney, Agent, or Firm—Oblon, Spivak, McClelland, Maier & Neustadt

[57] ABSTRACT

An antidiabetic composition which comprises a 7-thiaprostaglandin $E_1$ represented by the formula

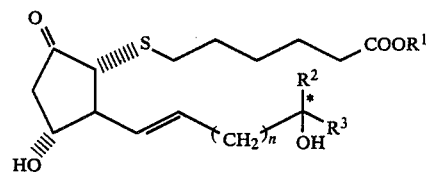

wherein $R^1$ is hydrogen atom, a straight-chain or branched-chain alkyl group or one equivalent of cation, $R^2$ is hydrogen atom or methyl group, $R^3$ is a straight-chain or branched-chain alkyl group or a cycloalkyl group, n is 0 or 1, and the asterisk represents an asymmtric carbon atom, which can be administered orally to exhibit the desired activity.

9 Claims, 1 Drawing Sheet

ANTIDIABETIC METHOD COMPRISING 7-THIAPROSTAGLANDIN $E_1$ OR ITS DERIVATIVES

BACKGROUND OF THE INVENTION

1. Field of the Invention

The present invention relates to antidiabetic composition comprising 7-thiaprostaglandin $E_1$ or its derivative as the active ingredient.

2. Description of the Prior Art

Prostaglandins have various physiological activities such as potent platelet aggregation inhibitory activity, vasodilating activity, hypotensive activity, gastric juice secretion inhibitory activity, smooth muscle contracting activity and diuretic activity and are substances which are useful for curing or preventing peripheral circulation disorders, myocardinal infarction, angina pectoris, arteriosclerosis, hypertension, gastric ulcer, duodenal ulcer, etc.

Of these prostaglandins, prostaglandins $E_1$ have recently attracted attention in respect of effects to improve peripheral circulation through their platelet aggregation inhibitory activity and vasodilating activity. Such compounds are clinically found useful for curing various diseases including Buerger's disease, arteriosclerosis obliterans and like arteriostenosis, ischemic ulcer and diabetic gangrene. Of these diseases, diabetic gangrene, which is one of the complications of diabetes, is though to be induced by the participation of factors associated with peripheral arteriosclerosis, diabetic microangiopathy, diabetric neuropathy, opportunistic infections and the like. Reports are made as to the efficacy of prostaglandins $E_1$ on diabetic gangrene (see Haruhiko Ninomiya et al., "Modern Medical Care," 15, 710–712, 1983; Ryuji Sano et al., "Modern Medical Care," 13, 142–148, 1981; Yasuhiro Oribe et al., "Diabetes," 24(8), 853–860, 1981; Haruhiko Nishima et al., "Prostaglandins—Advances in Clinical applications II," Gendai Iryosha, 228–231, 1985; Hiroyuki Hoshoshima et al., the same publication, 232–235, 1985; Nobuyuki Asakawa et al., the same publication, 236–241, 1985; Haruhito Nomoto et al., the same publication, 242–244, 1985; Hiroshi Hayashi et al., "Prostaglandins—Advances in Clinical applications," Gendai Iryosha, 165–173, 1983; and literature citing these reports). Effective cases of prostaglandins $E_1$ for diabetic neuropathy have also been recently reported (see Tsuguo Ebihara et al., "Prostaglandins Advances in Clinical Applications II," Gendai Iryosha, 245–248, 1985; Kenshin Kishida et al., the same publication, 249–256, 1985; Fumio Umeda et al., the same publication, 257–262, 1985; Tsutomu Nakamura et al., the same publication, 263–268, 1985; Atsuhiko Tada et al., the same publication, 269–273, 1985; Yasuhiro Oribe et al., "Prostaglandins—Advances in Clinical Applications III," Gendai Iryosha, 145–148, 1985; Hisaji Kamoi et al., the same publication, 149–154, 1985; Hiroyasu Dohgen et al., the same publication, 155–160, 1985; Kazuaki Orita et al., the same publication, 161–166, 1985; Kiyoshi Hashizume et al., the same publication, 167–169, 1985; and literature citing these reports).

In these reports, prostaglandins $E_1$ are used all as intravenous drips, and nothing has been reported as to a successful therapy with oral administration.

We have conducted intensive research on prostaglandins $E_1$ which are effective on diabetic neuropathy when administered orally and consequently found that the 7-thiaprostaglandins $E_1$ represented by the following formula (I) have the desired activity.

SUMMARY OF THE INVENTION

The present invention provides an antidiabetic composition comprising as the active ingredient a 7-thiaprostaglandin $E_1$ represented by the formula (I):

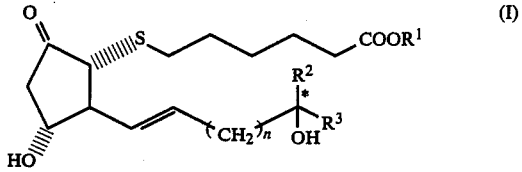

wherein $R^1$ is hydrogen atom, a straight-chain or branched-chain alkyl group or one equivalent of cation, $R^2$ is hydrogen atom or methyl group, $R^3$ is a straight-chain or branched-chain alkyl group or a cycloalkyl group, n is 0 or 1, and the asterisk represents an asymmetric carbon atom.

DETAILED DESCRIPTION OF THE INVENTION

Figure 1:
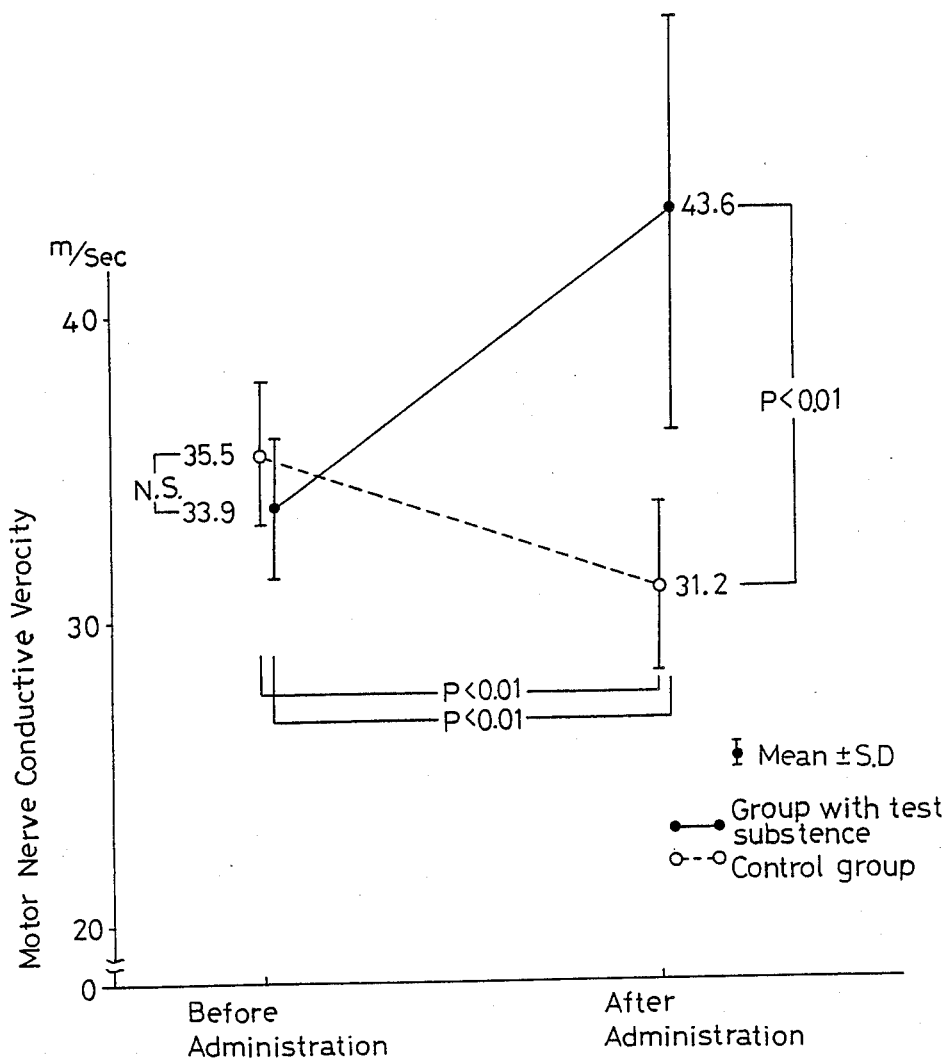
FIG. 1 is a graph showing the variation in nerve conduction velocity resulting from administration of a test substance for four weeks.

The antidiabetic composition of the present invention comprises 7-thiaprostaglandin $E_1$ or its derivative of the formula (I) as the active ingredient.

In the formula (I), examples of the straight-chain or branched-chain alkyl groups represented by $R^1$ are methyl, ethyl, n-propyl, isopropyl, n-butyl, sec-butyl, tert-butyl, n-pentyl, n-hexyl, n-heptyl, n-octyl, n-nonyl and n-decyl. Examples of useful cations (one equivalent) are alkali metal cations such as $Na^+$ and $K^+$, bivalent or trivalent metal cations such as $\frac{1}{2} Ca^{2+}$, $\frac{1}{2} Mg^{2+}$ and $\frac{1}{3} Al^{3+}$, ammonium cations such as ammonium ion and tetramethylammonium ion. Especially preferably as $R^1$ is hydrogen atom or methyl.

$R^2$ in the formula (I), which represents hydrogen atom or methyl, is preferably hydrogen when n is 0, or methyl when n is 1.

Examples of the straight-chain or branched-chain alkyl groups represented by $R^3$ in the formula (I) are alkyl groups having 1 to 10 carbon atoms such as ethyl, n-propyl, n-butyl, n-pentyl, n-hexyl, n-heptyl, n-octyl, n-decyl, 1-methylpentyl, 1-methylhexyl, 1,1-dimethylpentyl, 2-methylpentyl, 2-methylhexyl, 5-methylhexyl and 2,5-dimethylhexyl; preferably n-butyl, n-pentyl, n-hexyl and (R)-, (S)- or (RS)-2-methylhexyl; and more preferably 2-methylhexyl. Examples of the cycloalkyl groups are cyclopropyl, cyclobutyl, cyclopentyl, cyclohexyl, cycloheptyl and cyclooctyl, among which cyclopentyl and cyclohexyl are preferable.

When n in the formula (I) is 0, the formula represents either a 7-thiaprostaglandin $E_1$ which is represented by the formula (I-1):

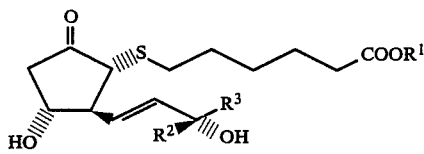
(I-1)

(wherein $R^1$, $R^2$ and $R^3$ are as defined above) and which has the same S-configuration as the natural-type configuration at the 15-position, or a 7-thiaprostaglandin $E_1$ which is represented by the formula (I-2):

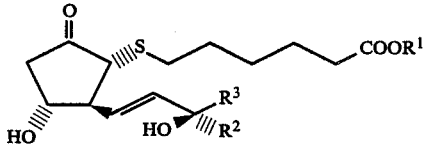
(I-2)

(wherein $R^1$, $R^2$ and $R^3$ are as defined above) and which has an unnatural-type configuration at the 15-position, or a mixture of these two types of prostaglandins $E_1$ in an optional ratio. When $R^2$ is hydrogen, 7-thiaprostaglandins $E_1$ are especially preferable which are represented by the formula (I-1) and having the natural-type configuration. The thiaprostaglandins of the formula (I) wherein n is 1 include those having R- or S-configuration at the 16-position and a mixture of these tow types of compounds in an optional ratio.

The antidiabetic composition of the present invention may comprises only one of these two kinds of the stereoisomers or a mixture of them in a desired ratio.

Preferred examples of 7-thiaprostaglandins $E_1$ for use in the antidiabetic composition of the invention are as follows.

(1) 7-Thiaprostaglandin $E_1$
(2) 16-Methyl-7-thiaprostaglandin $E_1$
(3) 20-Methyl-7-thiaprostaglandin $E_1$
(4) 17,20-Dimethyl-7-thiaprostaglandin $E_1$
(5) (17R) isomer of (4)
(6) (17S) isomer of (4)
(7) 15-Methyl-7-thiaprostaglandin $E_1$
(8) 16,16-Dimethyl-7-thiaprostaglandin $E_1$
(9) 16,17,18,19,20-Pentanor-15-cyclopentyl-7-thiaprostaglandin $E_1$
(10) 16,17,18,19,20-Pentanor-15-cyclohexyl-7-thiaprostaglandin $E_1$
(11) 15-Deoxy-16-hydroxy-16-methyl-7-thiaprostaglandin $E_1$ 278
(12) (16R) isomer of (11)
(13) (16S) isomer of (11)
(14) Methyl esters of (1) to (13)
(15) Ethyl esters of (1) to (13)
(16) Tert-butyl esters of (1) to (13)
(17) Sodium salts of (1) to (13)
(18) Potassium salts of (1) to (13)
(19) Magnesium salts of (1) to (13)
(20) Ammonium salts of (1) to (13)

The 7-thiaprostaglandins $E_1$ of the formula (I) can be prepared by known methods, which are disclosed in detail, for example, in Japanese Patent Unexamined Publication Nos. 108065/1982, 110562/1983 and 185761/1985 and Tanaka et al., "Chemical & Pharmaceutical Bulletin," Vol. 33, 2359 (1985). These methods can be represented generally by the following scheme.

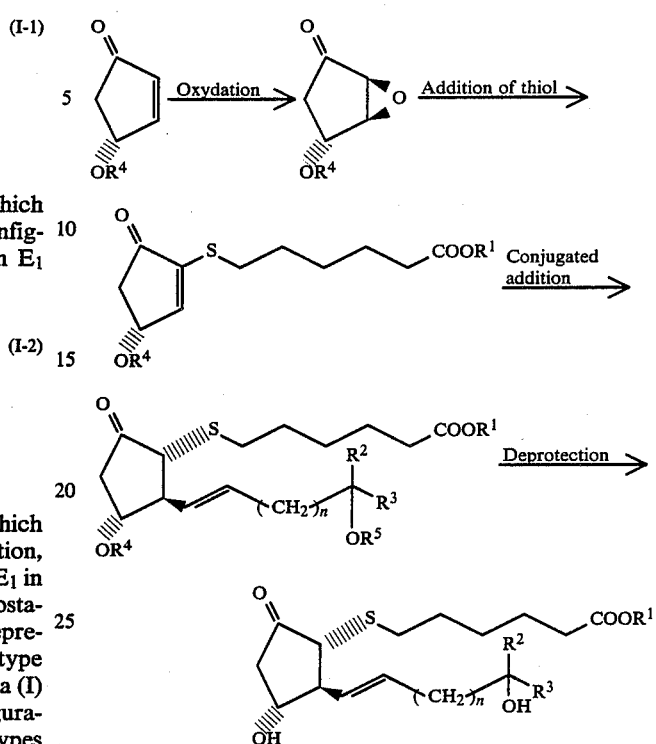

Thus, the thiaprostaglandins $E_1$ (I) per se are known compounds and are known to prevent or relieve thrombosis, angina pectoris, myocardinal infarction, arteriosclerosis, metastasis of malignant tumors, hypertension and the like through their platelet aggregation inhibitory activity, hypotensive activity and vasodilating activity. Nevertheless, the present invention has revealed for the first time that these compounds exhibit diabetes curing activity when orally administered.

Surprisingly, experiments on test animals with diabetes have revealed that the oral administration of 7-thiaprostaglandins $E_1$ (I) of the present invention is effective not only for the symptomatic therapy of diabetes in improving the nerve conduction velocity but also for the causal therapy of diabetes in reducing the blood sugar level. The antidiabetic composition of the invention can be administered for preventing and curing diabetic diseases such as corneal wound healing defects, cataract, diabetic neuropathy, retinopathy and nephropathy, especially for diabetic neuropathy.

For this purpose, the 7-thiaprostaglandins $E_1$ (I) can be given orally; or parenterally, e.g. intrarectally, subcutaneously, intramuscularly, intravenously or cutaneously. Preferably, these compounds are administered orally or intravenously.

For oral administration, the active ingredient can be made into solid preparations or liquid preparations. Examples of useful solid preparations are tablets, pellets, powder and granules. In formulating such solid preparations, the active ingredient is admixed with a pharmacologically acceptable carrier such as sodium bicarbonate, calcium carbonate, potato starch, sucrose, mannitol, carboxymethylcellulose or the like. While the preparation can be obtained by a conventional method, conjointly usable with such carriers are pharmaceutical additives such as lubricants including, for example, calcium stearate and magnesium stearate.

For example, an organic solvent or aqueous solution of an enteric substance, such as cellulose acetate phthalate, hydroxypropylmethylcellulose phthalate, polyvinyl alcohol phthalate, styrene-maleic anhydride copolymer or methacrylic acid-methyl methacrylate copolymer, can be sprayed onto the solid preparation to form an enteric coating thereon and obtain an enteric preparation. Powders, granules or like solid preparations can be enclosed with enteric capsules.

The liquid preparations for oral administration include, for example, emulsions, solutions, suspensions, syrups and elixirs. Such preparations contain a pharmacologically acceptable carrier which is generally used, e.g., water or liquid paraffin. Also usable as carriers are oily bases such as coconut oil, fractionated coconut oil, soybean oil and corn oil.

When required, the above mentioned preparations may contain auxiliary agent, perfume or flavoring agent, stabilizer or antiseptic which is usually used.

The liquid preparation may be given as encapsulated with an absorbable substance such as gelatin.

The solid preparation for intrarectal administration includes suppository containing the active ingredient and prepared by a known method.

The parenteral preparation is given in the form of aqueous or non-aqueous solution, suspension or emulsion as sterilized. The non-aqueous solution or suspension is prepared using a pharmacologically acceptable carrier such as propyl glycol, polyethylene glycol, olive oil or like vegetable oil, or ethyl oleate or like injectable organic ester. Auxiliary agents such as antiseptic, wetting agent, emulsifier, dispersant and stabilizer can be incorporated into such preparations. Such solution, suspension and emulsion can be sterilized by a suitable treatment, for example, by filtration with a bacteria retaining filter, addition of an antiseptic, or irradiation with ultraviolet rays. It is also possible to prepare a sterilized solid preparation and dissolve the preparation in sterilized water or sterilized injectable solvent immediately before use.

For cutaneous administration, for example ointments are useful which are prepared by a usual method.

The 7-thiaprostaglandins $E_1$ (I) of the invention are usable also in the form of its inclusion compound with $\alpha$-, $\beta$- or $\gamma$-cyclodextrin, methylated cyclodextrin or the like.

The 7-thiaprostaglandins $E_1$ of the invention, when to be used for curing diabetes, can be administered usually at a daily dosage of about 1 $\mu$g to about 1 mg for adults although the dosage varies with the symptoms, age, sex and body weight of the patient, route of administration, etc. The compound can be given in a single dose, or in several divided doses, e.g. two to six divided doses, per day.

The present invention will be described below with reference to the following test examples and examples.

TEST EXAMPLE 1

Test for Measuring Motor Nerve Conduction Velocity in Rats with Diabetes Induced by Streptozotocin Test animals and method Animals: Thirty 10-week-old male Spraque-Dawley rats (weighing about 300 g) were used. Twenty of these rats were intravenously given 45 mg/kg of streptozotocin in a single dose, as dissolved in a citric acid buffer having a pH of 4.5 to induce diabetes. A solution of test substance, i.e. methyl ester of (17R)-17,20-dimethyl-7-thiaprostaglandin $E_1$ in alcohol-saline was given to ten of the twenty rats with the induced diabetes at a dose of 0.3 mg/kg, calculated as the test substance (about 1 ml as the solution), once daily for 4 weeks using an intragastric administration tube. The same quantity of saline was given to the control group of ten rats and the remaining group of ten rats without the test substance, in the same manner as above. All the animals were reared in conventional cages in the usual manner, with no treatment conducted with insulin. In the meantime, one rat of the control group died of bronchial pneumonia, and six of the rats with diabetes died of a metabolic disorder due to the onset of idiopathic diabetes within one week after the administration of streptozotocin. Accordingly, the following evaluation test was conducted using nine rats as a control group, six rats without the test substance and eight rats with the test substance.

No significant change was observed physiologically or in general symptoms except that two rats with the test substance had soft feces. The control group gained weight slightly (from 302±7 g to 306±34 g), whereas the diabetic rats considerably diminished in weight with no significant difference observed between those with the test substance and those without the test substance (from 299±6 g to 244±18 g for the group with the test substance, and from 299±7 g to 241±15 g for the group without the test substance). Although the diabetic rats exhibited a significant increase in the glucose content of the plasma, the administration of the test substance for 4 weeks did not influence the glucose content (Table 2).

Electrophysiological test: The motor nerve conduction velocity was measured before the start of testing, and in the second week and fourth week using the left sciatic-posterior tibial nervous conduction system under pentobarbital anesthesia at a controlled temperature. The sciatic nerve was stimulated at a sciatic notch, and the tibial nerve of the ankle was checked for maximum stimulation with bipolar electrodes according to the method of A. K. Sharma et al. (J. Neurol. Sci., 1974; 23: 1–15). Table 1 shows the result.

TABLE 1

Variations in nerve conduction velocity due to administration of test substance to rats with streptozotocin-induced diabetes

| Animals | Motor nerve conduction velocity (m/sec) | | |
|---|---|---|---|
| | Week 0 | Week 2 | Week 4 |
| Control group (n = 9) | 51.4 ± 2.6 | 53.9 ± 3.1 | 56.5 ± 2.3 |
| Diabetic rats | | | |
| Without test substance (n = 6) | 51.9 ± 2.6 | 46.9 ± 2.3[b] | 46.5 ± 3.0[b,c] |
| With test substance (n = 8) | 51.5 ± 2.4 | 50.1 ± 3.7[a] | 50.5 ± 2.1[b] |

The value is expressed in mean ± SD.
[a]represents p 0.05 relative to the control
[b]represents p 0.001 relative to the control and
[c]stands for p 0.05 relative to the group with the test substance.

Measurement of sorbitol and myoinositol contents: On completion of the four-week test, both the sciatic nerves were immediately removed, weighed, homogenized in 8% perchloric acid (0.5 ml) and then subjected to ultra centrifugation at 3,000 rev/min for 10 minutes. The supernatant was neutralized with 2N aqueous solution of potassium hydroxide, and the sorbital content thereof was enzymatically measured according to the method of H. V. Bergmeyer et al. (Methods of enzymatic analysis, Academic Press, N.Y., pp. 1323-1326). The myoinositol content was determined by high-performance thin-layer chromatography (HPTLC) according to the method of J. Stepanek (J. Chromatogr., 1983; 257: 405-410). Table 2 shows the result.

TABLE 2

Plasma glucose content, sorbitol content and myoinositol content in rats with streptozotocin-induced diabetes

| Animals | Plasma glucose in week 4 (mg/dl) | Sorbitol (nmol/g wet weight) | Myoinositol (nmol/g wet weight) |
|---|---|---|---|
| Control group (n = 9) | 149.3 ± 15.5 | 138.7 ± 42.2 | 3.7 ± 0.7 |
| Diabetic rats | | | |
| Without test substance (n = 6) | 528.0 ± 74.8[a] | 508.5 ± 154.7[a] | 2.5 ± 0.3[a] |
| With test substance (n = 8)) | 565.5 ± 89.5[a] | 583.7 ± 125.5[a] | 2.8 ± 0.6[b] |

The value is expressed in mean ± SD.
[a]represents p 0.001 relative to the control, and
[b]represents p 0.01 relative to the control.

TEST EXAMPLE 2

Nerve Conduction Velocity Measurement and Glucose Tolerance Test for GK Rats with Spontaneous Diabetes Methyl ester of (17R)-17,20-dimethyl-7-thiaprostaglandin $E_1$ was tested for the effect to remedy the nervous disorder of GK rats with spontaneous diabetes. The animals were divided into two groups, one to which the test substance was given and the other without the test substance. Before testing, the animals were checked for glucose tolerance and nerve conduction velocity. The test substance was orally given at a dose of 0.3 mg/kg/day for 4 weeks, and the animals were then checked for glucose tolerance and nerve conduction velocity. Four weeks after the completion of the administration (8 weeks after the start of testing), the same checking procedures were repeated. FIG. 1 and Table 3 show the result.

Before the administration, there was no significant difference in glucose tolerance and nerve conduction velocity between the group with the test substance and the group without the test substance. The four-week administration of the test substance achieved a significant improvement in both glucose tolerance and nerve conduction velocity, but 4 weeks after the completion of administration, the former group was found to be at the same level as the latter in the glucose tolerance and nerve velocity owing to a significant decrease.

TABLE 3

Glucose tolerance test in GK rats with spontaneous diabetes

| Group | Before administration | After 4-week administration | 4 Weeks after administration |
|---|---|---|---|
| Without test substance | 1314.2 | 1436.2 | 1506.0 |
| With test substance | 1287.9 | 1022.8 | 1465.4 |

The sum of blood glocose values (mg/dl) before the tolerance test and 30, 60 and 120 minutes after giving glucose.

EXAMPLE 1

Tablets were prepared each with the following composition.

| | |
|---|---|
| Active ingredient | 100 μg or 500 μg |
| Lactose | 280 mg |
| Potato starch | 80 mg |
| Polyvinyl pyrrolidone | 11 mg |
| Magnesium stearate | 5 mg |

The active ingredient, lactose and potato starch were mixed together and uniformly wetted with 20% ethanol solution of polyvinyl pyrrolidone. The mixture was passed through a 20 mm-mesh screen, dried at 45° C. and passed through a 15 mm-mesh screen to obtain granules, which were then kneaded with magnesium stearate and compressed into tablets.

The active ingredient used was methyl ester of (17R)-17,20-dimethyl-7-thiaprostaglandin $E_1$ as a typical example.

EXAMPLE 2

Hard gelatin capsules were prepared each containing the following components.

| | |
|---|---|
| Active ingredient | 100 μg |
| Microcrystalline cellulose | 195 mg |
| Amorphous silicic acid | 5 mg |

The active ingredient in the form of fine particles, microcrystalline cellulose and unpressed amorphous silicic acid were thoroughly mixed together and packed into hard gelain capsules.

The active ingredient used was the same compound as used in Example 1 as a typical example.

EXAMPLE 3

The same compound as used in Example 1 was dissolved in fractionated coconut oil. The following encapsulating composition was made into a solution with heating and used for enclosing the active ingredient solution therewith in the usual manner by a soft capsule production machine to obtain soft capsules each containing 200 μg of the active ingredient.

| Encapsulating composition | |
|---|---|
| Gelatin | 10 parts by weight |
| Glycerin | 5 parts by weight |
| Sorbic acid | 0.08 parts by weight |
| Purified water | 14 parts by weight |

What is claimed is:

1. A method for treating a patient with diabetes, comprising orally administering an antidiabetic composition comprising as the active ingredient an antidiabetically effective amount of 7-thiaprostaglandin $E_1$ or its derivative represented by the formula (I):

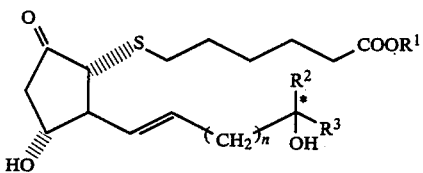

(I)

wherein $R^1$ is hydrogen atom, a straight-chain or branched-chain alkyl group or one equivalent of cation, $R^2$ is hydrogen atom or methyl group, $R^3$ is a straight-chain or branched-chain alkyl group or a cycloalkyl group, n is 0 or 1, and the asterisk represents an asymmetric carbon atom, in admixture with a carrier.

2. The method of claim 1, wherein $R^1$ is hydrogen atom or methyl group.

3. The method of claim 1, wherein $R^2$ is hydrogen atom.

4. The method of claim 1, wherein $R^3$ is a straight-chain or branched-chain alkyl group having 1 to 10 carbon atoms.

5. The method of claim 1, wherein $R^3$ is 2-methylhexyl group.

6. The method of claim 1, wherein n is 0.

7. The method of claim 1, wherein said asymmetric carbon atom represented by the asterisk has an absolute structure of S-configuration.

8. The method of claim 1, wherein said 7-thiaprostaglandin $E_1$ is the methyl ester of (17R)-17,20-dimethyl-7-thiaprostaglandin $E_1$.

9. The method of claim 1, wherein in said antidiabetic composition said active ingredient is present in an amount of about 1 µg to about 1 mg.

* * * * *

UNITED STATES PATENT AND TRADEMARK OFFICE
CERTIFICATE OF CORRECTION

PATENT NO. : 4,937,265

DATED : JUNE 26, 1990

INVENTOR(S) : TOSHIO TANAKA ET AL

It is certified that error appears in the above-identified patent and that said Letters Patent is hereby corrected as shown below:

Title Page:
In the abstract, line 3; the figure

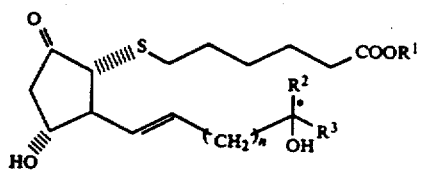

should read

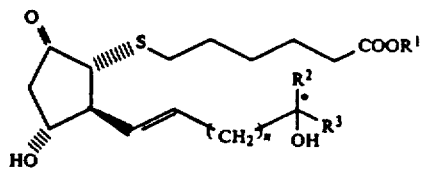

In column 2, lines 9-17; the figure

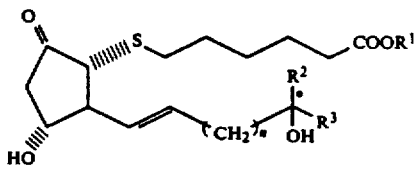

UNITED STATES PATENT AND TRADEMARK OFFICE
CERTIFICATE OF CORRECTION

PATENT NO. : 4,937,265

DATED : JUNE 26, 1990

INVENTOR(S) : TOSHIO TANAKA ET AL

It is certified that error appears in the above-identified patent and that said Letters Patent is hereby corrected as shown below:

should read

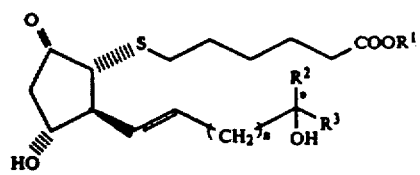

UNITED STATES PATENT AND TRADEMARK OFFICE
CERTIFICATE OF CORRECTION

PATENT NO. : 4,937,265

DATED : June 26, 1990

INVENTOR(S) : Toshio Tanaka et al

It is certified that error appears in the above-identified patent and that said Letters Patent is hereby corrected as shown below:

In Claim 1, line 6; the figure

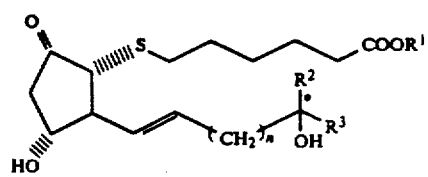

should read

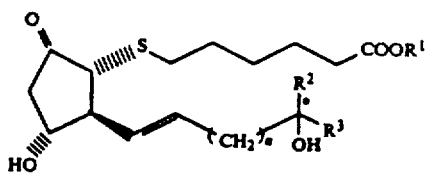

Signed and Sealed this

Seventeenth Day of November, 1992

Attest:

DOUGLAS B. COMER

Attesting Officer

Acting Commissioner of Patents and Trademarks